United States Patent [19]

Yamakawa et al.

[11] Patent Number: 5,693,823
[45] Date of Patent: Dec. 2, 1997

[54] PROCESS FOR PREPARING 1,1-DISUBSTITUTED-1H-BENZO[E]INDOLE COMPOUND AND HYDROXYL-SUBSTITUTED COMPOUND THEREOF

[75] Inventors: Katsuyoshi Yamakawa; Tadahisa Sato, both of Kanagawa, Japan

[73] Assignee: Fuji Photo Film Co., Ltd., Kanagawa, Japan

[21] Appl. No.: 798,054

[22] Filed: Feb. 11, 1997

[30] Foreign Application Priority Data

Feb. 16, 1996 [JP] Japan .................. HEI8-052592
Jul. 1, 1996 [JP] Japan .................. HEI8-171128

[51] Int. Cl.$^6$ .................................. C07D 209/56
[52] U.S. Cl. ................ 548/427; 546/276.7; 548/407
[58] Field of Search .................................. 548/427

[56] References Cited

U.S. PATENT DOCUMENTS 2,895,955  7/1959  Heseltine et al. .................. 548/427

FOREIGN PATENT DOCUMENTS 3272890  12/1991  Japan .
WO9507888  3/1995  WIPO .

OTHER PUBLICATIONS

*Angew. Chem. Int. Ed.*, vol. 6, No. 1. p. 84, (1967).
*J. Prakt. Chem.*, 78, 143 (1908).
Ikeda et al., Chemical Abstracts, 118:147460p (1993).

*Primary Examiner*—Fiona T. Powers
*Attorney, Agent, or Firm*—Sughrue, Mion, Zinn, Macpeak & Seas, PLLC

[57] ABSTRACT

A process for preparing a 1,1-disubstituted-1H-benzo[e] indole compound represented by formula (III) comprising reacting a 2-naphthol compound represented by formula (I), a carbonyl compound represented by formula (II), and a hydrazine compound in the presence of an acid catalyst, wherein $R^1$ represents a group capable of substituting a hydrogen atom on the naphthalene ring; m represents 0 or an integer of 1 to 6; $R^2$ and $R^3$ each represents an alkyl group, an aryl group or a heterocyclic group; and $R^4$ represents a hydrogen atom, an alkyl group, an aryl group or a heterocyclic group.

14 Claims, No Drawings

PROCESS FOR PREPARING 1,1-DISUBSTITUTED-1H-BENZO[E]INDOLE COMPOUND AND HYDROXYL-SUBSTITUTED COMPOUND THEREOF

FIELD OF THE INVENTION

This invention relates to a 1,1-disubstituted-1H-benzo[e]indole compound useful as an intermediate for synthesizing dyes.

BACKGROUND OF THE INVENTION 1,1-Disubstituted-1H-benzo[e]indole compounds are important as an intermediate for synthesizing photochromic compounds, cyanine dyes, etc. as disclosed in WO95/07888, U.S. Pat. No. 2,895,955, German Patent 2,046,141, JP-A-5-306282 (the term "JP-A" as used herein means an "unexamined published Japanese patent application), JP-A-5-306285, JP-A-6-202281, JP-A-4-283269, JP-A-3-272890, JP-A-2-110548, JP-A-1-113394, JP-A-1-106887, and JP-A-1-106888.

The above compounds have hitherto been synthesized via a 2-hydrazinonaphthalene or a derivative thereof as an intermediate in accordance with the Fischer's indole synthesis as shown below, but the process have many problems to be solved.

(Synthesis Example)

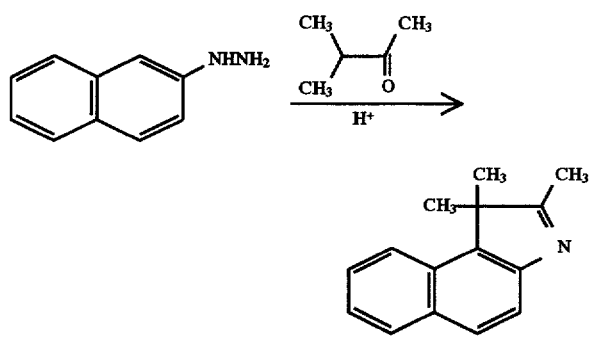

Firstly, 2-hydrazinonaphthalene and its derivatives are suspected of carcinogenicity and need care when produced in quantity.

Secondly, known processes for synthesizing 2-hydrazinonaphthalene or its derivative, which are shown below, are problematical.

(1) Diazotization of 2-naphthylamine and reduction (Ann., 232, 242 (1886), JP-A-3-272890):

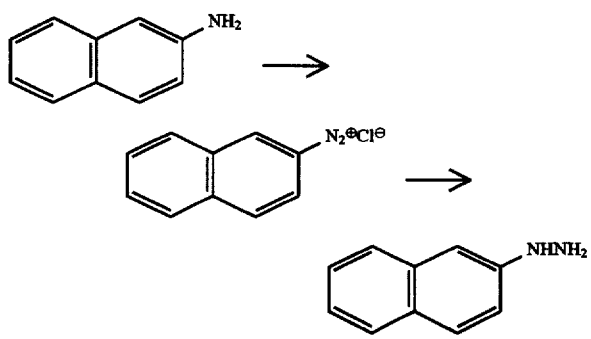

(2) Reaction between 2-naphthol and hydrazine in an autoclave (high temperature and high pressure reaction) (J. Prakt. Chem., 78, 143 (1908), WO95-07888):

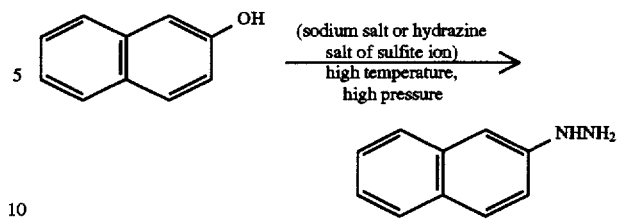

(3) Reaction with sodium hydrazide (Angew. Chem. Int. Ed. Engl., 6, 84 (1967)):

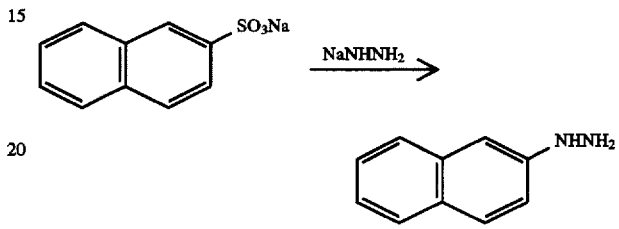

Process (1) starts with carcinogenic 2-naphthylamine, which requires extremely restricted handling, and naturally has an economical disadvantage.

Process (2) can be carried out at a reduced temperature because the reactivity of naphthol to hydrazine is improved by taking advantage of addition and release of a sulfite to and from naphthol. And yet the reaction should be performed in an autoclave at 120° to 130° C. for several hours. Co-existence of hydrazine and various metallic ions in an autoclave involves the danger of explosion, though depending on the material of the autoclave.

Process (3) is relatively easy to adopt in a laboratory, but sodium hydrazide is known to explode at 100° C. or above (Angew. Chem. Int. Ed. Engl., 3, 342 (1964)) and is difficult to use in large quantities.

On the other hand, while a hydroxyl-substituted 1,1-disubstituted-1H-benzo[e]indole compound is promising for ease of introducing a linking group according to a purpose, it is an unknown compound that has not heretofore been synthesized.

SUMMARY OF THE INVENTION

An object of the present invention is to provide an economical and safe process for preparing a 1,1-disubstituted-1H-benzo[e]indole compound without isolating a 2-hydrazinonaphthalene compound which is obtained by using an explosive or carcinogenic compound.

Another object of the present invention is to provide a novel hydroxyl-substituted 1,1-disubstituted-1H-benzo[e] indole compound which is promising for various applications.

In the light of the above objects, the inventors of the present invention have conducted extensive investigation and found as a result that the objects can be accomplished by the following means.

That is, the invention provides (1) a process for preparing a 1,1-disubstituted-1H-benzo[e]indole compound represented by formula (III):

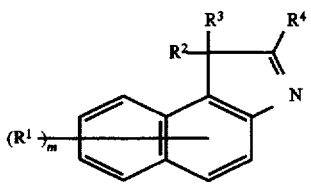

wherein $R^1$ represents a group capable of substituting a hydrogen atom on the naphthalene ring; m represents 0 or an integer of 1 to 6; when m is 2 or more, $R^1$'s may be the same or different; $R^2$ and $R^3$ each represents an alkyl group, an aryl group or a heterocyclic group; and $R^4$ represents a hydrogen atom, an alkyl group, an aryl group or a heterocyclic group, comprising reacting a 2-naphthol compound represented by formula (I):

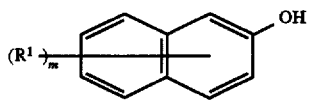

wherein $R^1$ and m are as defined above, a carbonyl compound represented by formula (II):

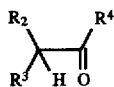

wherein $R^2$, $R^3$, and $R^4$ are as defined above, and a hydrazine compound in the presence of an acid catalyst.

The invention also provides (2) a hydroxyl-substituted 1,1-disubstituted-1H-benzo[e]indole compound represented by formula (IV):

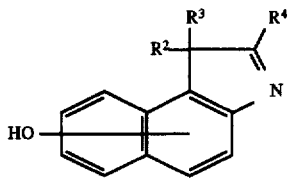

wherein $R^2$ and $R^3$ each represents an alkyl group, an aryl group or a heterocyclic group; and $R^4$ represents a hydrogen atom, an alkyl group, an aryl group or a heterocyclic group.

DETAILED DESCRIPTION OF THE INVENTION

In formulae (I) and (III), $R^1$ represents a group capable of substituting a hydrogen atom on the naphthalene ring, such as a halogen atom (e.g., fluorine, chlorine, bromine, and iodine), an alkyl group (e.g., methyl and t-butyl), an aryl group (e.g., phenyl and naphthyl), a carboxyl group, a cyano group, a carbamoyl group having 1 to 30 carbon atoms, preferably 1 to 15 carbon atoms (e.g., methylcarbamoyl and phenylcarbamoyl), a nitro group, an amino group (e.g., amino, N-methylamino and N,N-dimethylamino), an azo group having 1 to 30 carbon atoms, preferably 1 to 15 carbon atoms (e.g., phenylazo and naphthylazo), an acylamino group having 1 to 30 carbon atoms, preferably 1 to 15 carbon atoms (e.g., acetamido), a sulfonamido group having 1 to 30 carbon atoms, preferably 1 to 15 carbon atoms (e.g., methanesulfonamido), a ureido group, a hydroxyl group, an alkoxy group (e.g., methoxy), an aryloxy group (e.g., phenoxy), a sulfo group, and a sulfamoyl group having 0 to 30 carbon atoms, preferably 0 to 15 carbon atoms (e.g., methylsulfamoyl and phenylsulfamoyl).

The alkyl group (residual group) or the aryl group (residual group) as cited above for $R^1$ and for $R^2$, $R^3$ and $R^4$ hereinafter described may have such a substituent as has been cited above. The substituted or unsubstituted alkyl group preferably has 1 to 20 carbon atoms in total, and the substituted or unsubstituted aryl group preferably has 6 to 26 carbon atoms in total.

m represents 0 or an integer of 1 to 6, preferably 0.

In formulae (II), (III), and (IV), $R^2$ and $R^3$ each represents an alkyl group, an aryl group or a heterocyclic group, and $R^4$ represents a hydrogen atom, an alkyl group, an aryl group or a heterocyclic group.

The above-mentioned alkyl group (residual group) is preferably a straight-chain, branched or cyclic alkyl group having 1 to 20 carbon atoms, including methyl, ethyl, n-butyl, isobutyl, t-butyl and cyclohexyl groups.

The above-mentioned aryl group (residual group) is preferably an aromatic group having 6 to 20 carbon atoms, including phenyl and naphthyl groups.

The heterocyclic group is a cyclic group containing at least one hetero atom selected from a nitrogen atom, an oxygen atom, a sulfur atom, a selenium atom, and a tellurium atom and capable of bonding at a possible position thereof. The heterocyclic group is preferably 3- to 7-membered ring. Typical examples of such a heterocyclic group include 2-furyl, 4-pyridyl, 3-pyrazolyl, morpholino, and piperazino groups.

It is preferable that $R^2$, $R^3$, and $R^4$ all represent an alkyl group, especially a methyl group.

The hydrazine compound which can be used in the present invention includes anhydrous hydrazine, hydrazine hydrate, and a hydrazine salt, such as hydrazine hydrochloride and hydrazine sulfate. Hydrazine hydrate is particularly preferred.

The compound of formula (II) is preferably used in an amount of 0.5 to 3 mol, particularly 0.8 to 1.5 mol, per mole of the compound of formula (I).

The hydrazine compound is preferably used in an amount of 0.5 to 5 mol, particularly 0.8 to 3 mol, per mole of the compound of formula (I).

The acid catalyst which can be used in the present invention can be either a Bransted acid (i.e., a proton-donating acid) or a Lewis acid.

The proton-donating acid includes hydrochloric acid, sulfuric acid, phosphoric acid, organosulfonic acids (e.g., methanesulfonic acid, trifluoromethanesulfonic acid, benzenesulfonic acid, and p-toluenesulfonic acid), and organic carboxylic acids (e.g., acetic acid and benzoic acid).

The Lewis acid includes halides, alkoxides, and salts with, for example, trifluoromethanesulfonic acid or perchloric acid of boron, aluminum, titanium, tin, silicon, copper, zinc or a lanthanide.

The proton-donating acids are preferred. Still preferably, sulfuric acid, hydrochloric acid, methanesulfonic acid, trifluoromethanesulfonic acid, benzenesulfonic acid or p-toluenesulfonic acid is used.

The acid is preferably used in an amount of 0.9 to 3 mol, particularly 0.9 to 1.5 mol, per mole of the hydrazine compound.

The solvent which can be used in the reaction includes aromatic hydrocarbons (e.g., toluene, xylene and mesitylene), alcohols (e.g., ethanol and ethylene glycol), halogen-containing solvents (e.g., chlorobenzene and dichloromethane), organic carboxylic acids (e.g., acetic acid and propionic acid), amides (e.g., N-methylpyrrolidone and 1,3-dimethylimidazolidinone), and water. Preferred of them are aromatic hydrocarbons. The solvent is used in an amount usually of from 1 to 50 times, preferably of from 1 to 10 times, the weight of the compound of formula (I).

The reaction can be conducted in an aromatic hydrocarbon solvent while azeotropically removing water produced by means of Dean-Stark.

The reaction temperature ranges preferably from 80° to 200° C., more preferably 100° to 150° C. The reaction time is suitably 1 to 80 hours, preferably 4 to 50 hours, still preferably 10 to 30 hours. The reaction can be carried out under atmospheric pressure.

Typical examples of the compounds used in the process of the present invention and the compounds synthesized by the process of the present invention are shown below, but the present invention is not deemed to be limited thereto.

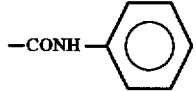

Formula (I)

| Compound | R¹ | m | Position of Substituent |
|---|---|---|---|
| (I)-1 | — | 0 | — |
| (I)-2 | Br | 1 | 6 |
| (I)-3 | OH | 1 | 4 |
| (I)-4 | OCH$_3$ | 1 | 7 |
| (I)-5 | OH | 1 | 5 |
| (I)-6 | OH | 1 | 3 |
| (I)-7 | OH | 1 | 6 |
| (I)-8 | OH | 1 | 7 |
| (I)-9 | NH$_2$ | 1 | 3 |
| (I)-10 | CO$_2$H | 1 | 3 |
| (I)-11 | CO$_2$H<br>OH | 2 | —3<br>—8 |
| (I)-12 | CO$_2$H<br>OH | 2 | —3<br>—6 |
| (I)-13 | —CONH—(phenyl) | 1 | 3 |
| (I)-14 | —CONH—(phenyl-OCH$_3$) | 1 | 3 |
| (I)-15 | CONH—(phenyl-OCH$_3$)<br>Br | 2 | —3<br>—6 |
| (I)-16 | CONH$_2$ | 1 | 3 |
| (I)-17 | CONHNH$_2$ | 1 | 3 |
| (I)-18 | CN | 1 | 6 |
| (I)-19 | SO$_3$Na | 1 | 3 |

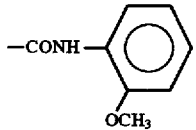

Formula (II)

| Compound | R² | R³ | R⁴ |
|---|---|---|---|
| (II)-1 | CH$_3$ | CH$_3$ | CH$_3$ |
| (II)-2 | CH$_3$ | CH$_3$ | H |
| (II)-3 | CH$_3$ | CH$_3$ | C$_2$H$_5$ |
| (II)-4 | CH$_3$ | CH$_3$ | C$_3$H$_7$ |
| (II)-5 | CH$_3$ | CH$_3$ | C$_4$H$_9$ |
| (II)-6 | CH$_3$ | C$_2$H$_5$ | CH$_3$ |
| (II)-7 | (R² and R³ are linked to form cyclopropane) | | CH$_3$ |

-continued

| | R² | R³ | R⁴ |
|---|---|---|---|
| (II)-8 | CH₃CH₂CH(CH₃)— | CH₃ | H |
| (II)-9 | C₉H₁₉ | CH₃ | H |
| (II)-10 | (R² and R³ are linked to form cyclohexane) | | H |
| (II)-11 | phenyl | phenyl | —CH₃ |
| (II)-12 | (R² and R³ are linked to form cyclohexane) | | phenyl |
| (II)-13 | (R² and R³ are linked to form cyclopropane) | | phenyl |
| (II)-14 | " | | 4-Cl-phenyl |
| (II)-15 | " | | 4-F-phenyl |
| (II)-16 | " | | 4-OCH₃-phenyl |
| (II)-17 | CH₃ | phenyl | H |
| (II)-18 | phenyl | phenyl | H |

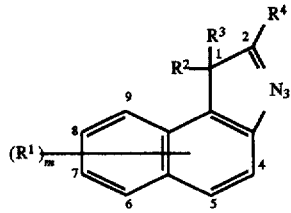

Formula (III)

| Compound | R¹ | m | Position of Substituent | R² | R³ | R⁴ |
|---|---|---|---|---|---|---|
| (III)-1 | — | 0 | — | CH₃ | CH₃ | CH₃ |
| (III)-2 | — | 0 | — | CH₃ | CH₃ | H |
| (III)-3 | — | 0 | — | CH₃ | CH₃ | C₂H₅ |
| (III)-4 | — | 0 | — | CH₃ | CH₃ | C₃H₇ |
| (III)-5 | — | 0 | — | CH₃ | CH₃ | C₄H₉ |
| (III)-6 | — | 0 | — | CH₃ | C₂H₅ | CH₃ |
| (III)-7 | — | 0 | — | (R² and R³ are linked to form cyclopropane) | | CH₃ |

-continued

| | | | | | | |
|---|---|---|---|---|---|---|
| (III)-8 | — | 0 | — | CH₃CH₂CH(CH₃)— | CH₃ | H |
| (III)-9 | — | 0 | — | C₉H₁₃ | CH₃ | H |
| (III)-10 | — | 0 | — | 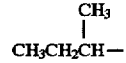 (R² and R³ are linked to form cyclohexane) | | H |
| (III)-11 | — | 0 | — |  | 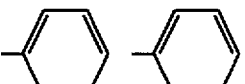 | —CH₃ |
| (III)-12 | — | 0 | — |  (R² and R³ are linked to form cyclohexane) | |  |
| (III)-13 | — | 0 | — | 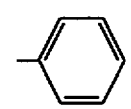 (R² and R³ are linked to form cyclopropane) | |  |
| (III)-14 | — | 0 | — | " | | 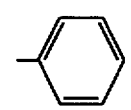 |
| (III)-15 | — | 0 | — | " | | 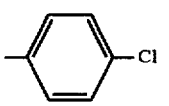 |
| (III)-16 | — | 0 | — | " | | 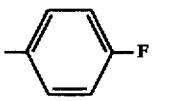 |
| (III)-17 | — | 0 | — | CH₃ | 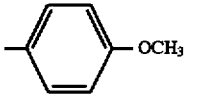 | H |
| (III)-18 | — | 0 | — |  |  | H |
| (III)-19 | Br | 1 | 7 | CH₃ | CH₃ | CH₃ |
| (III)-20 | Br | 1 | 7 | CH₃ | CH₃ | H |
| (III)-21 | Br | 1 | 7 |  |  | CH₃ |
| (III)-22 | Br | 1 | 7 | CH₃ |  | H |
| (III)-23 | OCH₃ | 1 | 8 | CH₃ | CH₃ | C₂H₅ |
| (III)-24 | OCH₃ | 1 | 8 | CH₃ | CH₃ | CH₃ |
| (III)-25 | OCH₃ | 1 | 8 | CH₃ | C₂H₅ | CH₃ |
| (III)-26 | OCH₃ | 1 | 8 |  |  | CH₃ |
| (III)-27 | NH₂ | 1 | 4 | CH₃ | CH₃ | CH₃ |
| (III)-28 | NH₂ | 1 | 4 | CH₃ | CH₃ | C₄H₉ |
| (III)-29 | NH₂ | 1 | 4 | CH₃ | CH₃ | H |

-continued

| | | | | | | |
|---|---|---|---|---|---|---|
| (III)-30 | NH$_2$ | 1 | 4 | 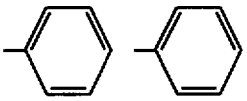 |  | H |
| (III)-31 | CO$_2$H | 1 | 4 | CH$_3$ | CH$_3$ | CH$_3$ |
| (III)-32 | CO$_2$H | 1 | 4 | CH$_3$ | CH$_3$ | C$_3$H$_7$ |
| (III)-33 | CO$_2$H | 1 | 4 | CH$_3$ | CH$_3$ | C$_4$H$_9$ |
| (III)-34 | CO$_2$H | 1 | 4 | CH$_3$ | C$_2$H$_5$ | CH$_3$ |
| (III)-35 | CONH$_2$ | 1 | 4 | CH$_3$ | CH$_3$ | CH$_3$ |
| (III)-36 | CONH$_2$ | 1 | 4 | C$_9$H$_{19}$ | CH$_3$ | H |
| (III)-37 | CONH$_2$ | 1 | 4 | 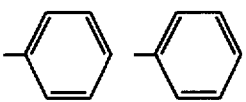 |  | CH$_3$ |
| (III)-38 | 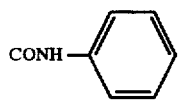CONH- | 1 | 4 | CH$_3$ | CH$_3$ | CH$_3$ |
| (III)-39 | 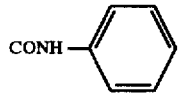CONH- | 1 | 4 | $\begin{array}{c}\text{CH}_3\\|\\\text{CH}_3\text{CH}_2\text{CH}-\end{array}$ | CH$_3$ | H |
| (III)-40 | 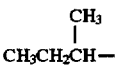CONH- | 1 | 4 | 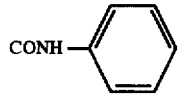 |  | H |
| (III)-41 | CN | 1 | 7 | CH$_3$ | CH$_3$ | CH$_3$ |
| (III)-42 | CN | 1 | 7 | 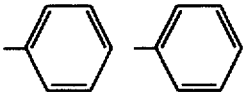 |  | H |
| (III)-43 | CN | 1 | 7 | CH$_3$ |  | H |
| (III)-44 | SO$_3$H | 1 | 4 | CH$_3$ | CH$_3$ | CH$_3$ |
| (III)-45 | SO$_3$H | 1 | 4 | 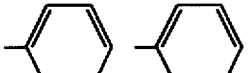 |  | CH$_3$ |
| (III)-46 | SO$_3$H | 1 | 4 | 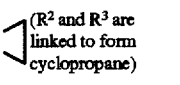 (R$^2$ and R$^3$ are linked to form cyclopropane) | |  |
| (III)-47 | OH | 1 | 6 | CH$_3$ | CH$_3$ | CH$_3$ |
| (III)-48 | OH | 1 | 7 | CH$_3$ | CH$_3$ | CH$_3$ |
| (III)-49 | OH | 1 | 8 | CH$_3$ | CH$_3$ | CH$_3$ |
| (III)-50 | OH | 1 | 4 | CH$_3$ | CH$_3$ | CH$_3$ |
| (III)-51 | OH | 1 | 6 | CH$_3$ | C$_2$H$_5$ | CH$_3$ |
| (III)-52 | OH | 1 | 7 | 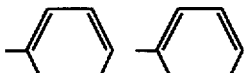 |  | H |
| (III)-53 | OH | 1 | 6 | CH$_3$ | CH$_3$ | C$_4$H$_9$ |
| (III)-54 | OH | 1 | 7 | CH$_3$ | CH$_3$ | 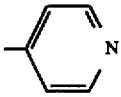 |

-continued

| Compound | | | | | | |
|---|---|---|---|---|---|---|
| (III)-55 | — | 0 | — | CH₃ | CH₃ | 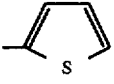 thiophene |
| (III)-56 | — | 0 | — | CH₃ | CH₃ | 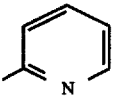 pyridine |
| (III)-57 | OCH₃ | 1 | 7 | C₂H₅ | C₂H₅ | C₂H₅ |

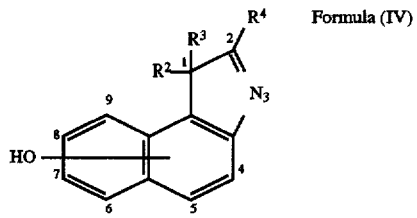

Formula (IV)

| Compound | Position of Substituent | R² | R³ | R⁴ |
|---|---|---|---|---|
| (IV)-1 (the same as compound (III)-47) | 6 | CH₃ | CH₃ | CH₃ |
| (IV)-2 (the same as compound (III)-48) | 7 | CH₃ | CH₃ | CH₃ |
| (IV)-3 (the same as compound (III)-49) | 8 | CH₃ | CH₃ | CH₃ |
| (IV)-4 (the same as compound (III)-50) | 4 | CH₃ | CH₃ | CH₃ |
| (IV)-5 | 6 | CH₃ | CH₃ | C₂H₅ |
| (IV)-6 (the same as compound (III)-53) | 6 | CH₃ | CH₃ | C₄H₉ |
| (IV)-7 | 6 | CH₃ | CH₃ | C₁₅H₃₁ |
| (IV)-8 | 6 | CH₃ | CH₃ | 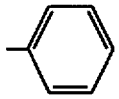 |
| (IV)-9 | 6 | CH₃ | CH₃ | 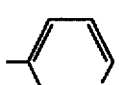 |
| (IV)-10 | 7 | CH₃ | CH₃ | H |
| (IV)-11 | 7 | CH₃ | CH₃ | C₂H₅ |
| (IV)-12 | 7 | CH₃ | CH₃ | 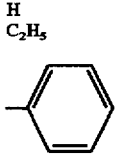 |
| (IV)-13 | 4 | C₂H₅ | C₄H₉ | CH₃ |
| (IV)-14 | 4 | CH₃ | CH₃ | C₁₅H₃₁ |
| (IV)-15 | 4 |  | CH₃ | CH₃ |
| (IV)-16 | 8 | CH₃ | CH₃ | 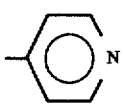 |
| (IV)-17 | 8 |  | CH₃ | CH₃ |
| (IV)-18 | 8 | CH₃ | CH₃ | C₉H₁₉ |
| (IV)-19 | 5 | CH₃ | CH₃ | CH₃ |

-continued

| | | | | |
|---|---|---|---|---|
| (IV)-20 | 5 | CH$_3$ | CH$_3$ | [phenyl] |
| (IV)-21 | 5 | CH$_3$ | C$_2$H$_5$ | CH$_3$ |
| (IV)-22 | 9 | CH$_3$ | CH$_3$ | CH$_3$ |
| (IV)-23 | 9 | [phenyl] | CH$_3$ | CH$_3$ |
| (IV)-24 | 9 | C$_6$H$_{13}$ | C$_8$H$_{17}$ | CH$_3$ |

The present invention will now be illustrated in greater detail with reference to Examples, but it should be understood that the present invention is not construed as being limited thereto.

EXAMPLE 1

Synthesis of compound (III-1) by reaction of compound (I)-1, compound (II)-1 and hydrazine compound:

In 20 ml of xylene were dissolved 1.44 g (0.01 mol) of compound (I)-1 and 0.95 g (0.011 mol) of compound (II)-1, and 2.47 g (0.013 mol) of p-toluenesulfonic acid was added to the solution. To the solution was further added 0.55 ml (0.011 mol) of hydrazine hydrate, and the solution was heated under reflux for 18 hours in a nitrogen atmosphere. After cooling, 20 ml of ethyl acetate and 20 ml of water were added, followed by liquid-liquid separation. The organic layer containing the residual compound (I)-1 was discarded. The aqueous layer was neutralized and made alkaline (pH: about 11) with a sodium hydroxide aqueous solution. To the aqueous solution was added 30 ml of ethyl acetate, followed by liquid-liquid separation and washing with water. Ethyl acetate was removed by evaporation, and the residue was crystallized from a methanol-water mixed solvent to give 0.31 g of crystals of compound (III)-1 in a yield of 15%. The spectrum of the compound agreed with that of an authentic sample.

$^1$H-NMR (300 MHz; CDCl$_3$) δ ppm: 1.55 (s, 6H), 2.40 (s, 3H), 7.43 (dd, 1H, J=8.3, 9.7 Hz), 7.55 (dd, 1H, J=8.3, 9.7 Hz), 7.78 (d, 1H, J=10.4 Hz), 7.84 (d, 1H, J=9.7 Hz), 7.93 (d, 1H, J=9.7 Hz), 8.02 (d, 1H, J=10.4 Hz).

MS (FAB (posi)): M+H: 210 (Mw: 209), 195.

While the yield wanted a further improvement, separation of the product from unreacted starting materials was easy, and isolation was simple. The reaction was followed by high-performance liquid chromatography and was found to produce little 2-naphthylhydrazine having suspected carcinogenicity (the compound was little found in the reaction mixture).

Other compounds represented by formula (III) can be synthesized in the same manner as described above.

EXAMPLE 2

Synthesis of Compound (III)-1 (under different conditions from Example 1)

In the same manner as in Example 1 except for replacing p-toluenesulfonic acid with the same molar amount of methanesulfonic acid, 0.37 g of compound (III)-1 was obtained in a yield of 18%.

EXAMPLE 3

Synthesis of Compound (III)-1 (under different conditions from Example 1)

In the same manner as in Example 1 except for replacing xylene with the same amount of toluene, 0.03 g of compound (III)-1 was obtained in a yield of 1.5%.

EXAMPLE 4

Synthesis of Compound (III)-1 (under different conditions from Example 1)

In the same manner as in Example 1 except for replacing xylene with the same amount of ethylene glycol, 0.15 g of compound (III)-1 was obtained in a yield of 7%.

EXAMPLE 5

Synthesis of Compound (III)-1 (under different conditions from Example 1)

In the same manner as in Example 4 except for replacing hydrazine hydrate with the same molar amount of hydrazine sulfate and replacing 0.013 mol of p-toluenesulfonic acid with 0.002 mol (0.1 ml) of sulfuric acid, 0.13 g of compound (III)-1 was obtained in a yield of 6%.

EXAMPLE 6

Synthesis of compound (III-1) (under different conditions from Example 1)

In 200 ml of xylene were dissolved 100.0 g (0.69 mol) of compound (I)-1 and 20.0 g (0.23 mol) of compound (II)-1, and 45.4 ml (0.69 mol) of methanesulfonic acid was added to the solution. To the solution was further added 23.1 ml (0.46 mol) of hydrazine hydrate under cooling with water. The mixture was stirred for 1 hour, and then heated at an oil bath temperature of 160° C. in a nitrogen atmosphere while removing water and xylene by means of Dean-Stark. After 13.5 ml of water was removed, the reaction was continued at an inner temperature of 135° C.±2° C. for 24 hours. The reaction mixture was cooled, and 420 ml of ethyl acetate and 225 ml of 4N hydrochloric acid aqueous solution were added thereto at 60° C. followed by stirring at room temperature for 30 minutes. After liquid-liquid separation, the organic layer was extracted with two 150 ml portions of 6N hydrochloric acid aqueous solution. The extract was combined with the aqueous layer and added dropwise to a mixture of 600 ml of a 25% sodium hydroxide aqueous solution and 500 ml of methanol under cooling with ice while keeping the inner temperature at 20° C. or below. The thus precipitated crystals were collected by filtration to give 30.0 g of compound (III)-1. The yield based on compound (II)-1 was 62.4%.

EXAMPLE 7

Synthesis of compound (III)-47 (the same as compound (IV)-1) by reaction of compound (I)-5, compound (II)-1 and hydrazine compound In 100 ml of mesitylene were dissolved 16.0 g (0.1 mol) of compound (I)-5 and 9.5 g (0.11 mol) of compound (II)-1, and 17 ml (0.26 mol) of methanesulfonic acid was added to the solution. To the solution was further added 11 ml (0.22 mol) of hydrazine hydrate, and the mixture was heated at an oil bath temperature of 160° C. for 15 hours in a nitrogen atmosphere. To the reaction mixture was added 200 ml of ethyl acetate, and the product was extracted three times from the organic layer with 4N hydrochloric acid aqueous solution. The combined aqueous layer was neutralized with sodium hydroxide, and ethyl acetate was added, followed by liquid-liquid separation. The organic layer was purified by silica gel column chromatography (n-hexane/ethyl acetate= 1/1) after concentrated and crystallized from an n-hexane/ ethyl acetate mixed solvent to give 1.78 g of compound (III)-47 (compound (IV)-1)) in a yield of 8%.

$^1$H-NMR (300 MHz; DMSO-$d_6$) δ ppm: 1.47 (s, 6H), 2.32 (s, 3H), 6.72 (d, 1H, J=8.3 Hz), 7.38 (dd, 1H, J=8.3, 8.3 Hz), 7.50 (d, 1H, J=8.3 Hz), 7.60 (d, 1H, J=8.3 Hz), 8.18 (d, 1H, J=8.3 Hz), 10.15 (s, 1H).

EXAMPLE 8

Synthesis of compound (III)-48 (the same as compound (IV)-2)) by reaction of compound (I)-7, compound (II)-1 and hydrazine compound In the same manner as in Example 7 except for replacing compound (I)-5 with compound (I)-7, 1.30 g of compound (III)-48 (compound (IV)-2)) was obtained (crystallizing solvent: acetonitrile) in a yield of 6%.

$^1$H-NMR (300 MHz; DMSO-$d_6$) δ ppm: 1.45 (s, 6H), 2.28 (s, 3H), 7.12–7.25 (m, 2H), 7.58 (d, 1H, J=9.2 Hz), 7.66 (d, 1H, J=9.2 Hz), 7.97 (d, 1H, J=9.2 Hz), 9.70 (s, 1H).

Comparative Example 1

The same procedure as in Example 1 was conducted except for using no p-toluenesulfonic acid. Compound (III) -1 was not obtained at all, and compound (I)-1 was recovered almost quantitatively. It was proved that the addition of an acid is important.

A 1,1-disubstituted-1H-benzo[e]indole compound useful as an intermediate for dyes, etc. can be synthesized in one pot by using inexpensive materials without involving substantial production of 2-naphthylhydrazine suspected of carcinogenicity.

While the invention has been described in detail and with reference to specific embodiments thereof, it will be apparent to one skilled in the art that various changes and modifications can be made therein without departing from the spirit and scope thereof.

What is claimed is:

1. A process for preparing a 1,1-disubstituted-1H-benzo [e]indole compound represented by formula (III):

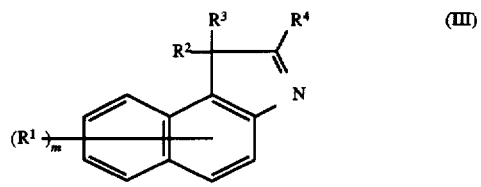

wherein $R^1$ represents a group capable of substituting a hydrogen atom on the naphthalene ring; m represents 0 or an integer of 1 to 6; when m is 2 or more, $R^1$'s may be the same or different; $R^2$ and $R^3$ each represents an alkyl group, an aryl group or a heterocyclic group; and $R^4$ represents a hydrogen atom, an alkyl group, an aryl group or a heterocyclic group, comprising reacting a 2-naphthol compound represented by formula (I):

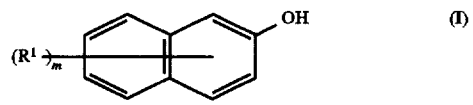

wherein $R^1$ and m are as defined above, a carbonyl compound represented by formula (II):

wherein $R^2$, $R^3$, and $R^4$ are as defined above, and a hydrazine compound in the presence of an acid catalyst.

2. A hydroxyl-substituted 1,1-disubstituted-1H-benzo[e] indole compound represented by formula (IV):

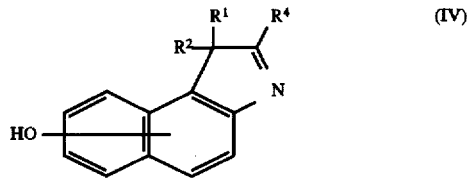

wherein $R^2$ and $R^3$ each represents an alkyl group, an aryl group or a heterocyclic group; and $R^4$ represents a hydrogen atom, an alkyl group, an aryl group or a heterocyclic group.

3. The process as claimed in claim 1, wherein the compound represented by formula (II) is used in an amount of from 0.5 to 3 mol per mole of the compound represented by formula (I).

4. The process as claimed in claim 3, wherein the compound represented by formula (II) is used in an amount of from 0.8 to 1.5 mol per mole of the compound represented by formula (I).

5. The process as claimed in claim 1, wherein the hydrazine compound is used in an amount of from 0.5 to 5 mol per mole of the compound represented by formula (I).

6. The process as claimed in claim 5, wherein the hydrazine compound is used in an amount of from 0.8 to 3 mol per mole of the compound represented by formula (I).

7. The process as claimed in claim 1, wherein the acid catalyst is selected from the group consisting of hydrochloric acid, sulfuric acid, phosphoric acid, organosulfonic acids, organic carboxylic acids, and halides, alkoxides, trifluoromethanesulfonates and perchlorates of boron, aluminum, titanium, tin, silicon, copper, zinc or a lanthanide.

8. The process as claimed in claim 7, wherein the acid catalyst is selected from the group consisting of sulfuric acid, hydrochloric acid, methanesulfonic acid, trifluoromethanesulfonic acid, benzenesulfonic acid and p-toluenesulfonic acid.

9. The process as claimed in claim 1, wherein the acid catalyst is used in an amount of from 0.9 to 3 mol per mole of the hydrazine compound.

10. The process as claimed in claim 9, wherein the acid catalyst is used in an amount of from 0.9 to 1.5 mol per mole of the hydrazine compound.

11. The process as claimed in claim 1, wherein the reaction temperature is from 80° C. to 200° C.

12. The process as claimed in claim 11, wherein the reaction temperature is from 100° C. to 150° C.

13. The process as claimed in claim 1, wherein the reaction time is from 1 to 80 hours.

14. The process as claimed in claim 13, wherein the reaction time is from 4 to 50 hours.

* * * * *